(12) United States Patent
Nakatani

(10) Patent No.: US 6,402,370 B1
(45) Date of Patent: Jun. 11, 2002

(54) THERMAL ANALYSIS APPARATUS

(75) Inventor: Rintaro Nakatani, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/558,616

(22) Filed: Apr. 26, 2000

(30) Foreign Application Priority Data

Apr. 27, 1999  (JP) .......................................... 11-119867

(51) Int. Cl.⁷ .............................................. G01N 25/00
(52) U.S. Cl. ...................................................... 374/14
(58) Field of Search ............................. 374/14, 10, 31

(56) References Cited

U.S. PATENT DOCUMENTS

| 3,902,354 | A | * | 9/1975 | Harlan et al. ............... 73/15 B |
| 5,346,306 | A | * | 9/1994 | Reading et al. ............... 374/10 |
| 5,788,373 | A | * | 8/1998 | Huetter et al. ................ 374/10 |
| 5,826,983 | A | * | 10/1998 | Nakamura et al. ........... 374/14 |
| 6,113,261 | A | * | 9/2000 | Blaine .......................... 374/14 |
| 6,146,012 | A | * | 11/2000 | Nakamura et al. ........... 374/10 |
| 6,210,035 | B1 | * | 4/2001 | Nakamura ..................... 374/11 |

* cited by examiner

Primary Examiner—Diego Gutierrez
Assistant Examiner—Mirellys Jagan
(74) Attorney, Agent, or Firm—Adams & Wilks

(57) ABSTRACT

A thermal analyzer is capable of separating a baseline component, a convex peak component and a concave peak component. During concave peak separation, arithmetic symbol inversion is performed by an arithmetic symbol inverter and separation into basic peaks is performed by basic peak optimization. Arithmetic symbol inversion is performed after separation by a second arithmetic symbol inverter. During convex peak separation, no arithmetic symbol inversion is performed.

28 Claims, 4 Drawing Sheets

6 Temperature adjust means
7 Physical amount fetch means
8 Temperature fetch means
9 Baseline separation means a
10 Arithmetic symbol inverter A
11 Basic peak model function generation means
12 Basic peak optimizing means a
13 Arithmetic symbol inverter B
14 Combining means
15 Output means 6 Temperature adjust means
7 Physical amount fetch means
8 Temperature fetch means
9 Baseline separation means a
10 Arithmetic symbol inverter A
11 Basic peak model function generation means
12 Basic peak optimizing means a
13 Arithmetic symbol inverter B
14 Combining means
15 Output means 6 Temperature adjust means
7 Physical amount fetch means
8 Temperature fetch means
14 Combining means
15 Output means
20 Baseline separation means b
21 Basic peak model function generation means for convex-formed peak components
22 Basic peak optimizing means b
23 Basic peak model function generation means for concave-formed peak components

THERMAL ANALYSIS APPARATUS

BACKGROUND OF THE INVENTION

The present invention relates to thermal analysis apparatuses.

In thermal analysis, analysis in which individual peaks are extracted from data having a plurality of peaks overlapped therein has been conventionally made. In a known method, parameters are sequentially varied in a plurality of basic peak model functions given by a curve-fitting method, or a Gaussian function, or the like, in a spectrum analysis such as spectroscopy, to optimize a spectrum measured.

It is satisfactory in every spectrum analysis to analyze data above a baseline, i.e. convex-formed peaks. However, there are often cases encountered in techniques of thermal analysis (DSC or DTA) in which convex-formed peaks and concave-formed peaks exist in the same data.

In such case it has been a conventional practice to cut out only convex-formed peaks to separate peaks or give up separation itself.

The above problem that the present invention is intended to solve, is solved by providing a thermal analysis apparatus that can separate respective peaks into basic peaks even where convex-formed peaks and concave-formed peaks exist in the same data.

SUMMARY OF THE INVENTION

The present invention has been developed in order to solve the above problem, and has constituent components comprising temperature control means, temperature measuring means, physical amount measuring means, thermal analysis data, baseline separation means, basic peak separation means and output means.

EXPLANATION OF THE REFERENCE NUMERALS AND SYMBOLS

Figure 1:
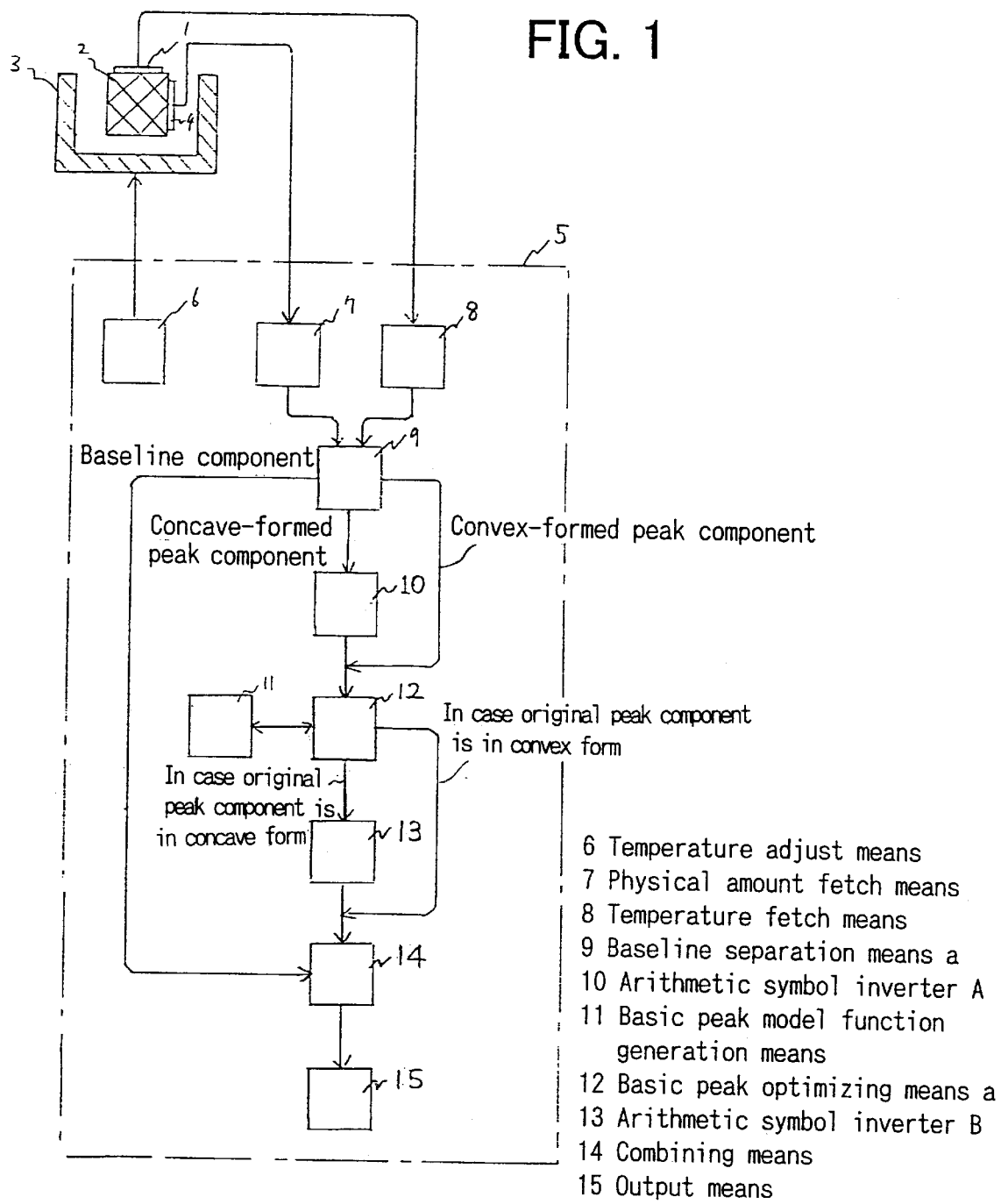
FIG. 1 is a block diagram showing an embodiment of the present invention.

1 Temperature sensor
2 Sample
3 Heater/cooler
4 Physical amount sensor
5 Computer a
6 Temperature adjust means
7 Physical amount fetch means
8 Temperature fetch means
9 Baseline separation means a
10 Arithmetic symbol inverter A
11 Basic peak model function generation means
12 Basic peak optimizing means a
13 Arithmetic symbol inverter B
14 Combining means
15 Output means
16 Heat generation peak
17 Baseline
18 Heat absorption peak
19 Computer b
20 Baseline separation means b
21 Basic peak model function generation means for convex-formed peak components
22 Basic peak optimizing means b
23 Basic peak model function generation means for concave-formed peak components

DESCRIPTION OF THE INVENTION

Hereunder, one embodiment of this invention will be explained based on the drawings.

FIG. 1 is a block diagram in the embodiment of the present invention. In FIG. 1 a computer 5 is a personal computer, workstation or the like provided with a user interface, such as a key board, mouse and CRT. This computer 5 has hardware and software to realize temperature adjusting means 6, physical amount acquisition means 7, temperature acquisition means 8, baseline separation means 9, first arithmetic symbol inverter 10, basic peak model function generation means 11, basic peak optimizing means 12, second arithmetic symbol inverter 13, combining means 14, and output means 15.

Temperature control means is realized by a heater/cooler 3 and temperature adjusting means 6. Similarly, temperature measuring means is realized by a temperature sensor 1 and temperature acquisition means 8, physical amount measuring means is realized by a physical sensor 4 and physical amount acquisition means 7, basic peak separation means is realized by first arithmetic symbol inverter 10 and basic peak model function generation means 11 and basic peak optimizing means 12 and second arithmetic symbol inverter 13, and combining output means by a combining means 14 and an output means 15.

First, a utilizer places a sample 2 in the heater/cooler 3. The utilizer interacts with the computer 5 to deliver a proper temperature program to the temperature adjusting means 6. The temperature adjusting means 6 controls the heater/cooler 3 to make a desired temperature change. The temperature sensor 1 measures a temperature of the sample 2 or around the sample 2, and a result thereof is fetched by the temperature acquisition means 8. The physical amount sensor 4 measures a change in a physical amount on the sample 2 due to temperature change or time, and a result thereof is fetched by the physical amount acquisition means 7. The physical amount sensor 4, if DSC, measures a change of a heat amount flowing into/out of the sample 2, if TC, a weight change of the sample 2, and, if TMA, a shape change of the sample 2. The physical amount and temperature fetched by the temperature acquisition means 8 and physical amount acquisition means 7 are made into thermal analysis data having a physical amount as a temperature or time function to be sent to the baseline separation mans 9.

In the baseline separation means 9, the thermal analysis data is separated into a baseline component and a peak component.

Figure 2:
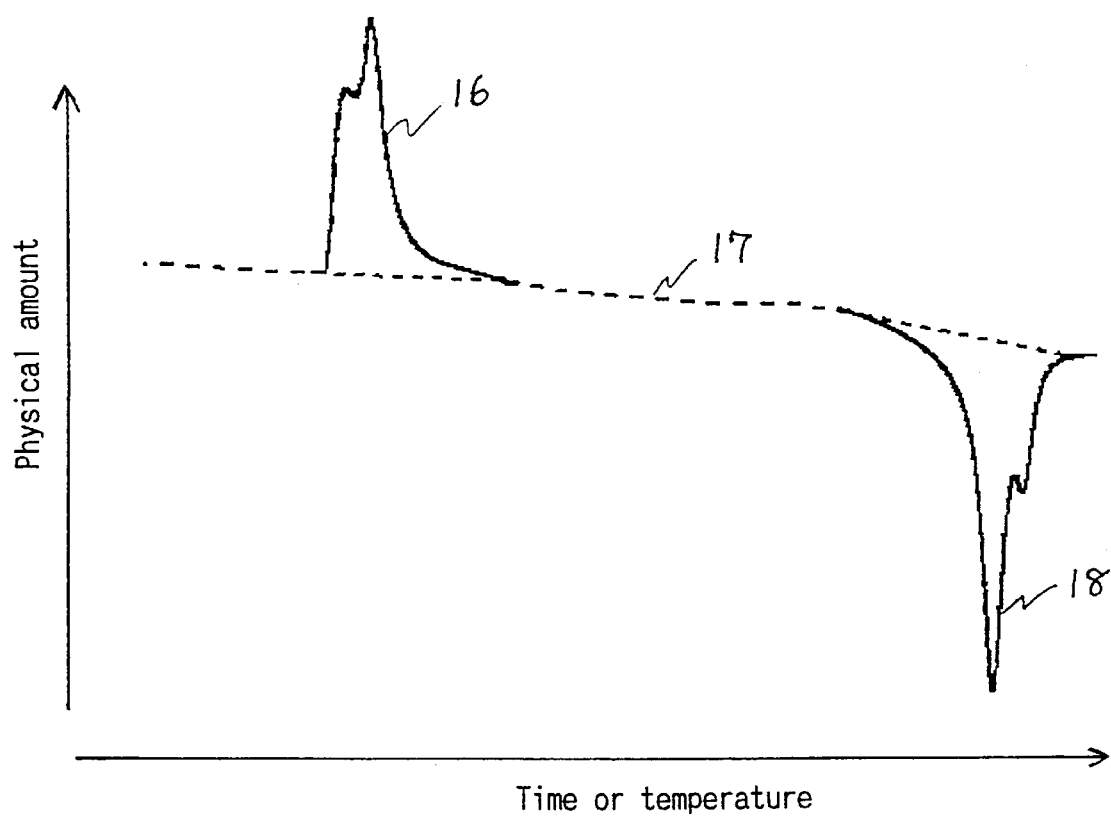
FIG. 2 is an explanatory view of a heat generation peak, heat absorption peak and baseline of the present invention.

In conventional thermal analysis, a baseline is taken by a succession of dots on a temperature or time axis where a physical amount change is in a steady state, a data departure from which is taken as a peak. In the case of DSC, a base line is taken by a succession of dots where a change of heat flowing into/out of the sample with respect to a reference substance is in a steady-state. Assuming that data increases greater than the baseline when heat flows out of the sample, data decreases less than the baseline when heat flows into the sample. In the case of fixing a rule of data increase and decrease with the baseline in this manner, a reaction of heat of from a steady state to a sample heat generation and again to the steady state is recorded as a convex-formed peak on the baseline 17 in the thermal analysis data as in a heat generation peak 16 in FIG. 2. Also, a reaction of heat of from the steady state to sample heat absorption and again to a steady state is recorded as a concave-formed peak on the baseline 17 as in a heat absorption peak 18 in FIG. 2.

The baseline separation means 9 is used to separate the thermal analysis data into a baseline component, a convex-formed peak component and a concave-formed peak component, respectively. The convex-formed peak component and the concave-formed peak component are subtracted physical amount data of the baseline component from the physical amount data of the thermal analysis data. Due to this, the physical amount of the concave-formed peak component assumes a negative value. Also, it is assumed that the baseline is properly set from a sample, measurement technique and measurement conditions. The setting method for a baseline may be conducted by any of the following.

(1) The utilizer provides curve fitting. The method includes a method of designating respective ends of a peak component on the measurement data by straight lines, a method of designating points on the measurement data and making a approximation between the dots by a spline function, a method of freely drawing a baseline irrespective of measurement data, and so on.

(2) Automatic setting is made by software. Measurement data is retrieved to extract data-stabilized points. The dots are functionally approximated to be set as a baseline. Also, a method may be used that data-stable points are used directly as a baseline and data-unstable, or peak component, regions are functionally approximated.

(3) The data measured on a sample that is thermally stable without change is directly used as a baseline.

The baseline component separated by the baseline separation means 9 is sent to the combining means 14. The concave-formed peak component is sent to the first arithmetic symbol inverter 10 and the convex-formed peak component to the basic peak optimizing means 12.

The first arithmetic symbol inverter 10 inverts the arithmetic symbol of a physical amount of the concave-formed peak component and supplies a result thereof to the basic peak optimizing means 12. In general, the basic peak model functions representing basic peaks, such as a Gauss function or Lorenz function, generates only a positive value of a function value. Due to this, the concave-formed peak component cannot be adapted for optimization to a basic peak model function. Accordingly, the concave-formed peak component in physical value is converted to a positive value by the first arithmetic symbol inverter 10 whereby the basic peak model function can be optimized into a concave-formed peak component.

The basic peak model function generation means 11 is a basic peak generation means. A basic peak is generated by providing parameters to the basic peak model function, such as the Gauss function or Lorenz function. The parameters, if for a Gauss function, are three parameters of peak position, peak height and width at half maximum. By handling these parameters an arbitrary-formed basic peak can be generated. Also, it is possible to select different basic peak model functions for respective basic peaks.

The basic peak optimizing means 12 separates the sent convex-formed peak component and arithmetic-symbol-inverted concave-formed peak component into a plurality of basic peaks. The method for separation is conducted by sequentially varying parameters of a plurality of basic peaks generated by the basic peak model function generation means 11, optimizing the peak component. The method for optimization uses a generally-known Davidon Fletcher Powell method, Simplex method, Gauss-Newton method or the like. In order to enhance optimization, devising may be used in this means that intrinsic components in the peak component are removed and the intrinsic components are added after optimization. The intrinsic components include fixed values, high-order functions, etc. The optimized plurality of basic peaks are sent to the second arithmetic symbol inverter 12 where the original peak component is in a concave form, or to the combining means 14 where the original peak component is in a convex form.

The second arithmetic symbol inverter 13 performs arithmetic symbol inversion on the sent basic peak. Due this, the basic peak turns into a concave form similar to the original concave-formed-peak component. After arithmetic symbol inversion, the basic peak is sent to the combining means 14.

The combining means 14 is used to combine the basic peak with a baseline component. The method for combining may be by any one or all of the followings.

(1) Addition of each basic peak and a baseline.

(2) The basic peak is synthesized on a basis of a calculation-source peak component and further added with the baseline.

A result of combining is sent the output means 15.

The output means 15 is used to visualize or record the combining result. All the combined results may be output or an addition result of one basic peak with a baseline may be output.

Figure 3:
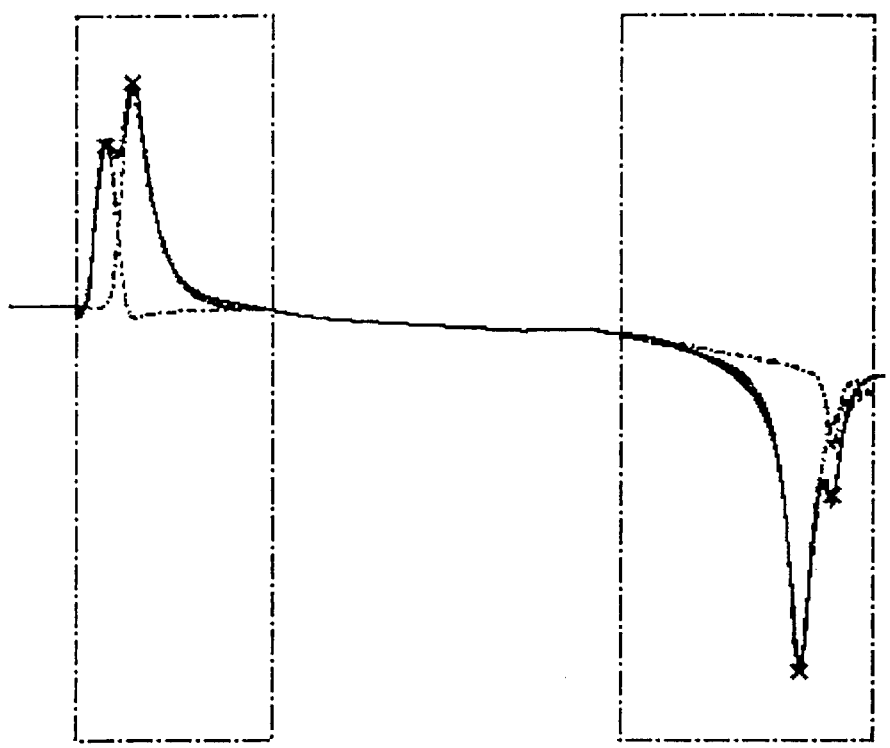
FIG. 3 is an output example in the embodiment of the present invention.
Figure 4:
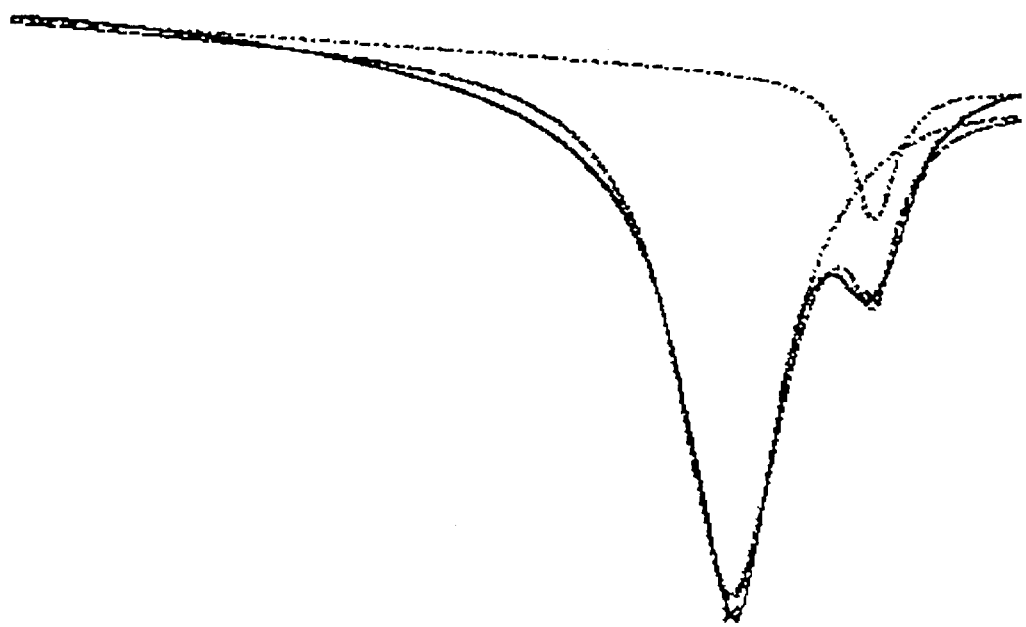
FIG. 4 is a concave-formed peak component partial magnifying view in the output example of the embodiment of the present invention.

Output examples in the above embodiment are shown in FIG. 3 and FIG. 4. FIG. 3 is a simultaneous separation example of a convex-formed peak and a concave-formed peak. FIG. 4 is a magnified figure of a concave-formed peak portion in the same example. In the figures, the solid line is thermal analysis data, and the one-dot chain line is an addition of each basic peak and a base line and the basic peak is synthesized on a basis of a peak component as a calculation source, and further added with the baseline.

Next, another embodiment of the present invention will be explained.

Figure 5:
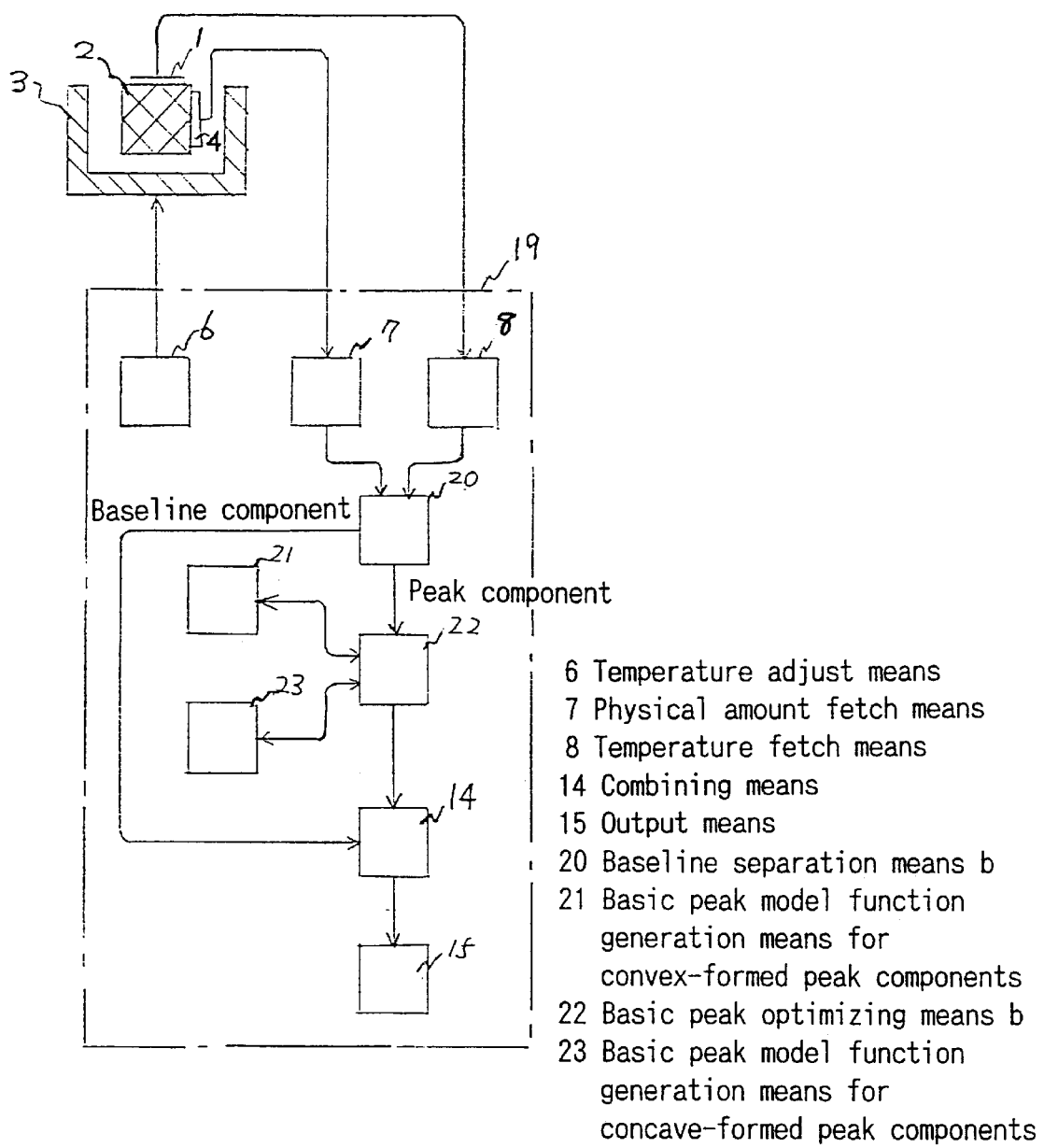
FIG. 5 is a block diagram showing another embodiment of the present invention.

FIG. 5 is a block diagram of another embodiment according to the invention. In FIG. 5 a temperature sensor 1, a sample 2, a heater/cooler 3, a physical amount fetch means 4, temperature adjust means 6, physical amount fetch means 7, temperature fetch means 8, combining means 14, output means 15, are the same as those of FIG. 1.

A computer 19 is a similar computer to the computer 5 in FIG. 1, but differs from the computer 5 with respect to a connection destination of an incorporated baseline separation means and in a method of realizing a peak separation means.

A baseline separation means 20 has the same function as the baseline separation means 9 but is different in a peak component result output destination. The baseline separation means 20 merely outputs a peak component to the basic peak optimizing means 22, but does not change an output destination depending on a peak shape unlike the baseline separation means 9.

In FIG. 5, the method of making possible separation of a concave-formed peak component into a basic peak does not perform arithmetic symbol inversion as made in FIG. 1, and is provided as a basic peak generation means a basic peak model function generation means 21 for convex-formed peak components and a basic peak model function generation means 23 for concave-formed peak components.

The basic peak model function generation means 21 for convex-formed peak components is similar in function to the basic peak model function generation means 11 in FIG. 1, and generates a positive function value.

A basic peak model function generation means 23 for concave-formed peak components is similar in function to the basic peak model function generation means 11, but generates a value inverted in arithmetic symbol, or negative function value. Specifically, for a Gauss function for example, the basic peak model function generation means 21 for convex-formed peak components generates a function value by the following formula.

$$y = h \cdot \exp(-\ln(2) \cdot (x-xc)^2/w^2)$$

y: function value (physical amount)
h: peak height (physical amount)
x: individual variable (temperature or time)
xc: peak position (temperature or time)
w: width at half maximum (temperature or time)

Similarly, for the Gauss function, the basic peak model function generation means 23 for concave-formed peak components generates a function value by the following formula.

$$y = -h \cdot \exp(-\ln(2) \cdot (x-xc)^2/w^2)$$

y: function value (physical amount)
h: peak height (physical amount)
x: individual variable (temperature or time)
xc: peak position (temperature or time)
w: width at half maximum (temperature or time)

The basic peak optimizing means b22 selectively use the basic peak model function generation means 21 for convex-formed peak components and the basic peak model function generation means 23 for concave-formed peak components according to a form of a peak component sent from the baseline separation means b20, and performs optimization similarly to the basic peak optimizing means a12 and sends a result thereof to the combining means 14.

Using the above function, the other embodiment of FIG. 5 can realize a thermal analysis apparatus having a similar effect to the embodiment of FIG. 1.

The present invention is structured using separation means to separate a convex-formed peak and a concave-formed peak. Accordingly, even where a convex-formed peak and a concave-formed peak exist in same data, the respective peak can be separated into basic peaks.

What is claimed is:

1. A thermal analysis apparatus, comprising:
   temperature control means for controlling a temperature of a sample;
   temperature measuring means for detecting a temperature of the sample or temperature in a vicinity of the sample;
   physical amount measuring means for detecting a variation in a physical characteristic of the sample with a temperature change of the sample or time to produce thermal analysis data in which the physical characteristic is represented as a function of at least one of sample temperature and time;
   baseline separation means for separating the thermal analysis data into a baseline component, a convex peak component and a concave peak component;
   basic peak separation means for separating overlapping peaks in the convex peak component and concave peak component into a plurality of basic peaks; and
   combining output means for combining and outputting the baseline component and the basic peaks.

2. A thermal analysis apparatus according to claim 1; wherein the basic peak separation means inverts the concave peak component before and after separating overlapping peaks.

3. A thermal analysis apparatus according to claim 1; wherein the basic peak separation means performs arithmetic symbol inversion on a basic peak model function when a peak component to be separated is in a concave form.

4. A thermal analysis apparatus according to claim 1; wherein the temperature control means comprises a heater and temperature adjusting means for adjusting the heater.

5. A thermal analysis apparatus according to claim 1; wherein the temperature measuring means comprises a temperature sensor and temperature acquisition means for acquiring a measured temperature from the temperature sensor.

6. A thermal analysis apparatus according to claim 1; wherein the physical amount measuring means comprises a physical characteristic sensor and physical characteristic acquisition means for acquiring a measured physical characteristic from the physical characteristic sensor.

7. A thermal analysis apparatus according to claim 1; wherein the baseline separation means performs baseline separation by one of a method of designating respective ends of a peak component on the thermal analysis data by straight lines, a method of designating points on the thermal analysis data and making a approximation between the points by a spline function, and a method of freely drawing a baseline irrespective of measurement data.

8. A thermal analysis apparatus according to claim 1; wherein the basic peak separation means comprises a first arithmetic symbol inverter for inverting a concave peak component before peak separation is performed, a basic peak model function generation means for generating a basic peak model function, basic peak optimizing means for optimizing peak separation, and a second arithmetic symbol inverter for inverting a concave peak component after peak separation is performed.

9. A thermal analysis apparatus according to claim 8; wherein the baseline component separated by the baseline separation means is supplied to the combining output means, the concave peak component is supplied to the first arithmetic symbol inverter, and the convex peak component is supplied to the basic peak optimizing means.

10. A thermal analysis apparatus according to claim 9; wherein the first arithmetic symbol inverter inverts the concave peak component and supplies a result thereof to the basic peak optimizing means so that the basic peak model function can be optimized by the basic peak optimizing means into a concave peak component, and an output of the basic peak optimizing means is supplied to the second arithmetic symbol inverted.

11. A thermal analysis apparatus according to claim 10; wherein the basic peak model function generated by the peak model function generation means is a Gaussian function or a Lorenz function.

12. A thermal analysis apparatus according to claim 11; wherein the basic peak optimizing means separates the received convex peak component and inverted concave peak component into a plurality of individual peaks.

13. A thermal analysis apparatus according to claim 12; wherein the basic peak optimizing means performs separation by sequentially varying parameters of a plurality of basic peaks generated by the basic peak model function generation means and optimizing the peak component using one of a Davidon Fletcher Powell method, a Simplex method, and a Gauss-Newton method.

14. A thermal analysis apparatus according to claim 13; wherein the basic peak optimizing means extracts intrinsic components including fixed values and high-order functions in the peak component, and reintroduces the intrinsic components after performing optimization to enhance optimization.

15. A thermal analysis apparatus according to claim 14; wherein the optimized plurality of individual peaks output by the basic peak optimizing means are sent to the second arithmetic symbol inverter when an original peak component is in a concave form, and to the combining output means when the original peak component is in a convex form.

16. A thermal analysis apparatus according to claim 15; wherein the second arithmetic symbol inverter inverts the received individual concave peak so that the individual peak takes on a concave form similar to the original concave peak component, and supplies the individual peak to the combining output means.

17. A thermal analysis apparatus according to claim 1; wherein the combining output means adds each individual peak and a baseline.

18. A thermal analysis apparatus according to claim 1; wherein the combining output means synthesizes each individual peak based on a calculation-source peak component, and adds the synthesized individual peak to the baseline.

19. A thermal analysis apparatus according to claim 1; wherein the combining output means displays or records the combined results.

20. A thermal analysis apparatus according to claim 19; wherein all combined results are output, or an addition result of one basic peak with a baseline is output.

21. A method of performing thermal analysis comprising the steps of:
heating a sample to obtain thermal analysis data in which a physical characteristic of a sample is represented as a function of at least one of time and sample temperature;
separating the thermal analysis data into a baseline component, a convex peak component and a concave peak component; and
separating overlapping peaks in the peak components into a plurality of individual peaks.

22. A method of performing thermal analysis according to claim 21; further comprising the steps of combining the baseline component and corresponding peak components; and outputting the combined baseline and peak components.

23. A method of performing thermal analysis according to claim 21; wherein the step of separating the thermal analysis data comprises the step of performing baseline separation by one of designating respective ends of a peak component on the thermal analysis data by straight lines, designating points on the thermal analysis data and making a approximation between the points by a spline function, and a method of freely drawing a baseline irrespective of measurement data.

24. A method of performing thermal analysis according to claim 21; wherein the step of performing the separation of the overlapping peaks comprises the steps of inverting a concave peak component before peak separation, generating a basic peak model function, optimizing peak separation using the basic peak model function, and inverting a concave peak component after peak separation.

25. A method of performing thermal analysis according to claim 24; wherein the concave peak component is inverted before being optimized to enable optimizing the basic peak model function into a concave peak component.

26. A method of performing thermal analysis according to claim 25; wherein the step of generating a basic peak model function comprises generating a Gaussian function or a Lorenz function.

27. A method of performing thermal analysis according to claim 26; wherein the step of optimizing comprises sequentially varying parameters of a plurality of basic peaks of the basic peak model function and optimizing the peak component using one of a Davidon Fletcher Powell method, a Simplex method, and a Gauss-Newton method.

28. A method of performing thermal analysis according to claim 27; further comprising the steps of extracting intrinsic components including fixed values and high-order functions in the peak component, and reintroducing the intrinsic components after performing optimization to enhance optimization.

* * * * *